(12) United States Patent
Ibeling

(10) Patent No.: US 9,387,073 B2
(45) Date of Patent: Jul. 12, 2016

(54) DELIVERY DEVICE DISTAL SHEATH CONNECTOR

(71) Applicant: St. Jude Medical, Cardiology Division, Inc., St. Paul, MN (US)

(72) Inventor: John Ibeling, Otsego, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 527 days.

(21) Appl. No.: 13/753,077

(22) Filed: Jan. 29, 2013

(65) Prior Publication Data

US 2014/0214151 A1    Jul. 31, 2014

(51) Int. Cl.
*A61F 2/24* (2006.01)
*A61F 2/966* (2013.01)

(52) U.S. Cl.
CPC .............. *A61F 2/2427* (2013.01); *A61F 2/966* (2013.01)

(58) Field of Classification Search
CPC ......... A61F 2/24; A61F 2/2427; A61F 2/966; A61F 2/95; A61F 2/2418; A61F 2/2433; A61F 2/2436; A61M 29/00
USPC ...................................... 623/1.11, 1.12, 2.11
See application file for complete search history.

(56) References Cited

U.S. PATENT DOCUMENTS

| | | | |
|---|---|---|---|
| 3,657,744 A | 4/1972 | Ersek | |
| 4,423,730 A | 1/1984 | Gabbay | |
| 5,415,664 A | 5/1995 | Pinchuk | |
| 5,843,167 A | 12/1998 | Dwyer et al. | |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,306,141 B1 | 10/2001 | Jervis | |
| 6,623,518 B2 | 9/2003 | Thompson et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,311,730 B2 | 12/2007 | Gabbay | |
| 7,476,244 B2 * | 1/2009 | Buzzard et al. | 623/1.11 |
| 7,510,572 B2 | 3/2009 | Gabbay | |
| 7,682,390 B2 | 3/2010 | Seguin | |
| 7,803,185 B2 | 9/2010 | Gabbay | |
| 2003/0050694 A1 | 3/2003 | Yang et al. | |
| 2004/0210304 A1 | 10/2004 | Seguin et al. | |

(Continued)

FOREIGN PATENT DOCUMENTS

| | | | |
|---|---|---|---|
| EP | 1053722 A2 | 11/2000 | |
| EP | 1129744 A1 | 9/2001 | |

(Continued)

OTHER PUBLICATIONS

Ruiz, Carlos, Overview of PRE-CE Mark Transcatheter Aortic Valve Technologies, Euro PCR, dated May 25, 2010?

(Continued)

*Primary Examiner* — Victor Nguyen
(74) *Attorney, Agent, or Firm* — Lerner, David, Littenberg, Krumholz & Mentlik, LLP

(57) ABSTRACT

A connector for coupling a distal sheath to an inner shaft of a medical delivery device includes a wedge defining a lumen for accepting the inner shaft of the medical delivery device and a cylindrical ring sized to mate with the wedge. The wedge may be welded or otherwise fixed to the inner shaft. The wedge and the ring are configured to be pressed together and lock a portion of the distal sheath therebetween.

18 Claims, 7 Drawing Sheets

(56) References Cited

U.S. PATENT DOCUMENTS

| | | |
|---|---|---|
| 2005/0137695 A1 | 6/2005 | Salahieh et al. |
| 2005/0137697 A1 | 6/2005 | Salahieh et al. |
| 2006/0074484 A1 | 4/2006 | Huber |
| 2006/0106415 A1 | 5/2006 | Gabbay |
| 2006/0142848 A1 | 6/2006 | Gabbay |
| 2006/0167468 A1 | 7/2006 | Gabbay |
| 2006/0172571 A1* | 8/2006 | Montena .............. H01R 9/0518 439/91 |
| 2006/0259120 A1 | 11/2006 | Vongphakdy et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0239271 A1 | 10/2007 | Nguyen |
| 2007/0244552 A1 | 10/2007 | Salahieh et al. |
| 2008/0071369 A1 | 3/2008 | Tuval et al. |
| 2008/0147182 A1 | 6/2008 | Righini et al. |
| 2009/0054975 A1 | 2/2009 | del Nido et al. |
| 2009/0306539 A1* | 12/2009 | Woodruff et al. ............. 600/561 |
| 2010/0004740 A1 | 1/2010 | Seguin et al. |
| 2010/0286768 A1 | 11/2010 | Alkhatib |
| 2010/0298931 A1 | 11/2010 | Quadri et al. |
| 2011/0224678 A1 | 9/2011 | Gabbay |
| 2012/0078352 A1 | 3/2012 | Wang et al. |

FOREIGN PATENT DOCUMENTS

| | | |
|---|---|---|
| EP | 1157673 A2 | 11/2001 |
| WO | 9523008 A1 | 8/1995 |
| WO | 2007071436 A2 | 6/2007 |
| WO | 2008070797 A2 | 6/2008 |
| WO | 2010051025 A1 | 5/2010 |
| WO | 2010087975 A1 | 8/2010 |

OTHER PUBLICATIONS

Quaden et al., "Percutaneous aortic valve replacement: resection before implantation", pp. 836-840, European J. of Cardio-thoracic Surgery, 27 (2005).

International Search Report and Written Opinion for Application No. PCT/US2014/012322 dated May 22, 2014.

* cited by examiner

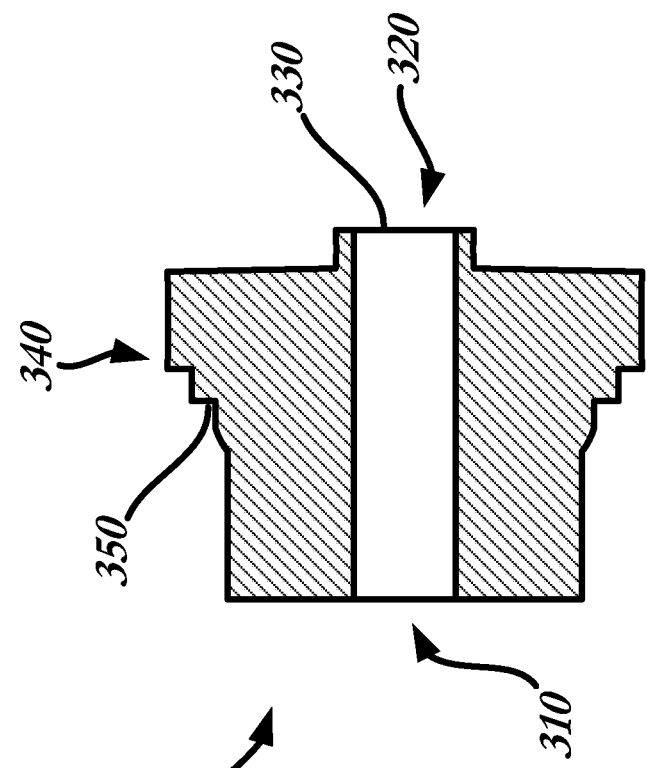
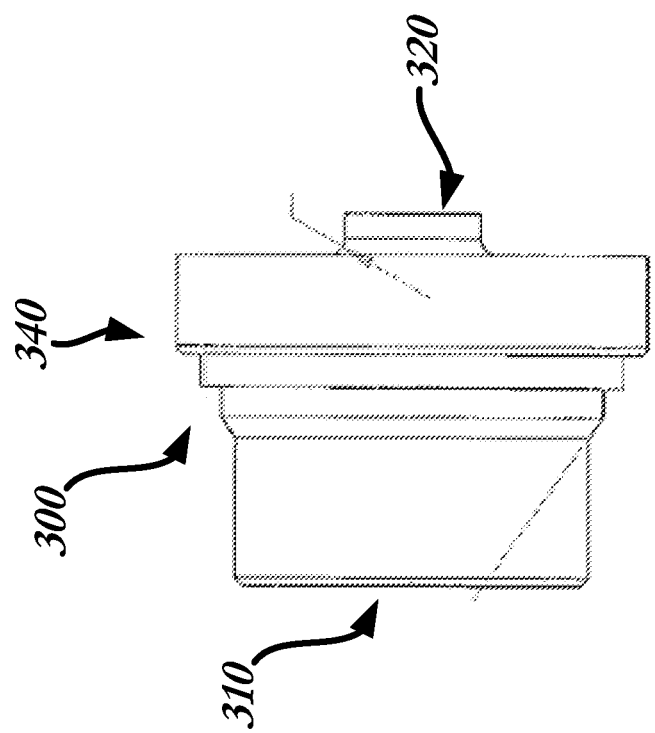
FIG. 4B
FIG. 4A

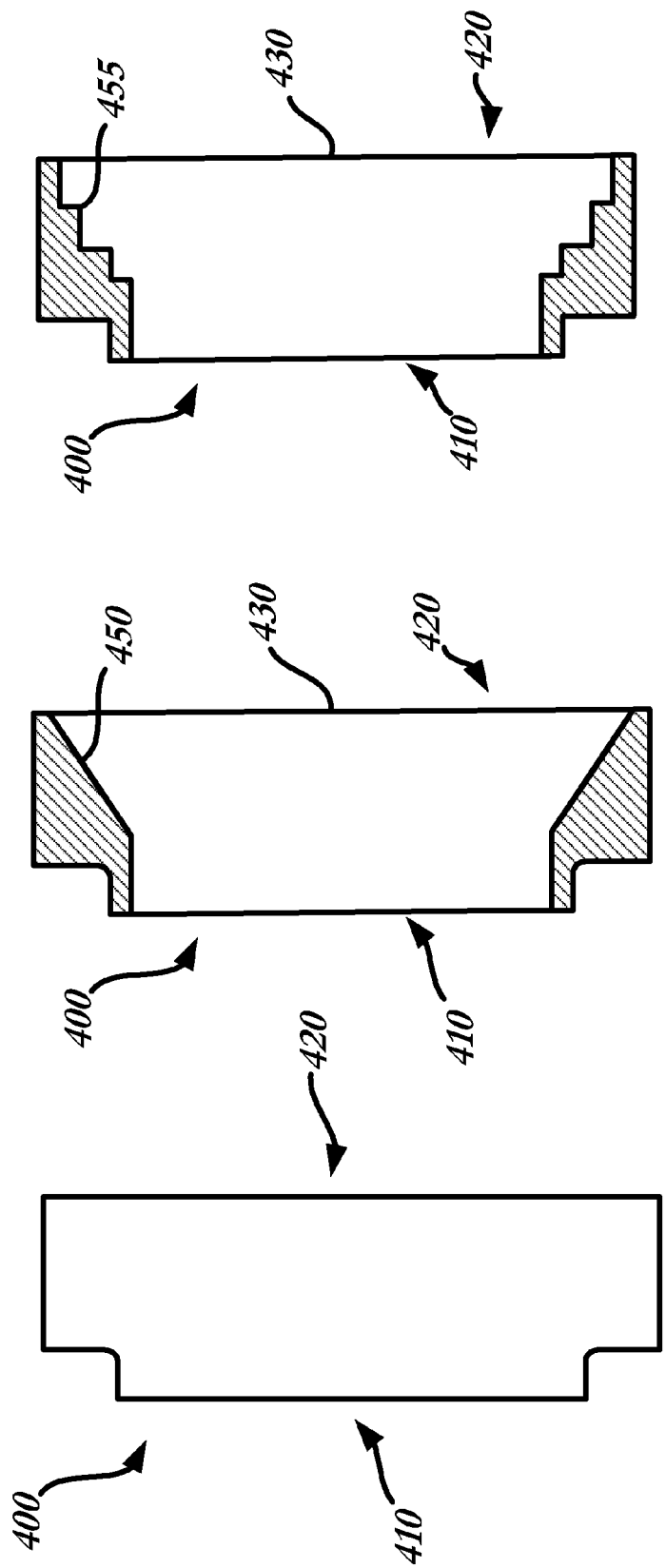

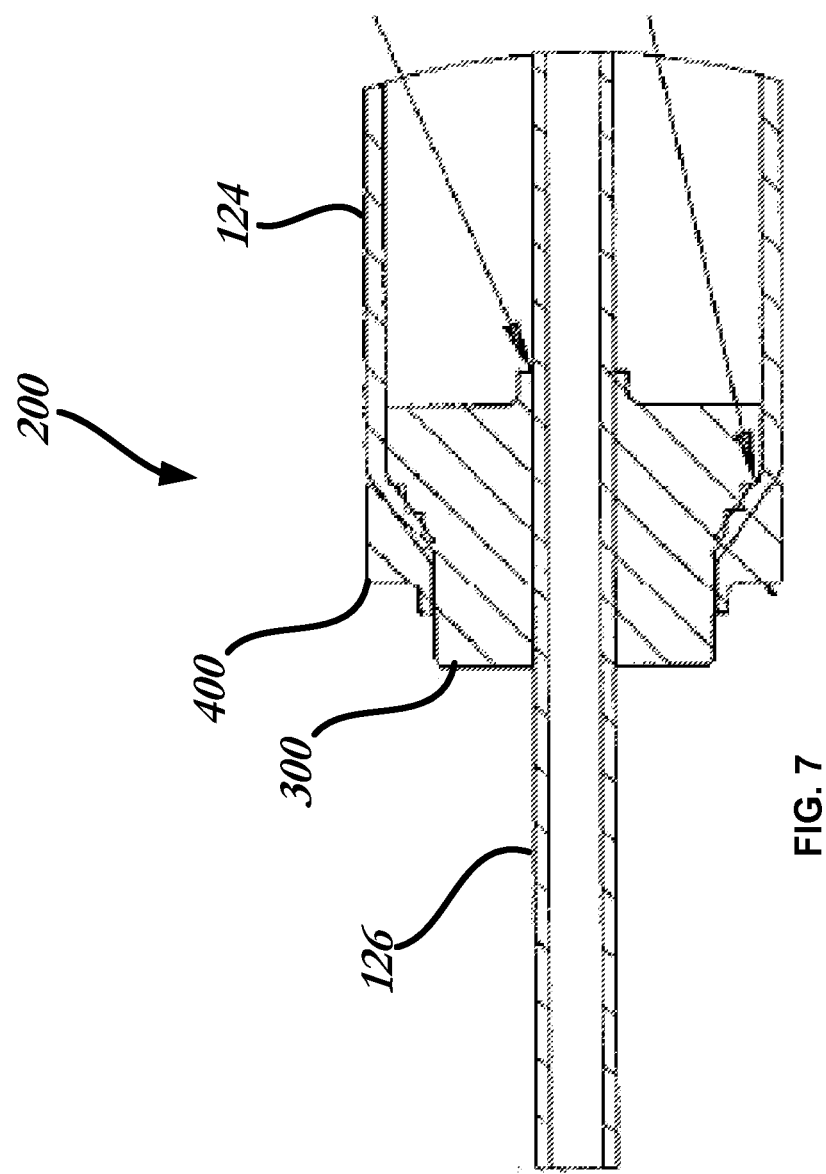

DELIVERY DEVICE DISTAL SHEATH CONNECTOR

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheaths the annulus end of the valve, so that the valve can be repositioned while in a collapsed state. After the valve has been repositioned, the user can fully release the valve.

Once a self-expanding valve has been fully deployed, it expands to a diameter larger than that of the sheath that previously contained the valve in the collapsed condition, making resheathing impossible or difficult at best. In order for the user to be able to resheath a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in some delivery devices for self-expanding valves, inner connections of the delivery device are prone to failure and may be unduly bulky.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

A delivery device for a collapsible prosthetic heart valve and a method of delivering a collapsible prosthetic heart valve in a patient are disclosed.

In some embodiments, a connector for coupling a distal sheath and an inner shaft of a medical delivery device includes a wedge defining a lumen for accepting the inner shaft of the medical delivery device, at least a portion of the wedge having an outer diameter sized to be received in the distal sheath. The connector further includes a cylindrical ring sized to be disposed over the distal sheath and at least the portion of the wedge. Engagement of the cylindrical ring with the wedge sandwiches the distal sheath between at least the portion of the wedge and the cylindrical ring.

In some examples, the wedge may include a cylindrical body and a cone portion. The cone portion of the wedge may include a series of annular steps having increasing diameters. The wedge may include a biocompatible metal. The wedge may include stainless steel. The ring may define an outwardly tapering lumen configured to receive the steps of the wedge. The ring and the wedge may include the same metal. The wedge may be welded to the inner shaft and the wedge and the ring may be welded together. The distal sheath may be inwardly tapered at a portion sandwiched between the wedge and the ring.

In some embodiments, a method of coupling a distal sheath and an inner shaft of a delivery device includes providing a connector having a wedge defining a lumen for accepting the inner shaft of the medical delivery device, at least a portion of the wedge having an outer diameter sized to be received in the distal sheath and a cylindrical ring sized to be disposed over the distal sheath and at least the portion of the wedge. A portion of the distal sheath may be positioned between the wedge and the ring of the connector. The wedge may be coupled to the inner shaft and the ring so as to sandwich the distal sheath between at least the portion of the wedge and the cylindrical body.

In some examples, the coupling step includes laser welding the wedge to the inner shaft. The coupling step may include laser welding the ring to the wedge. The method may further include thermoforming the portion of the distal sheath prior to positioning the portion of the distal sheath between the wedge and the ring. The thermoforming step may include inwardly tapering the portion using a tipping machine. The method may further include clamping the wedge and the ring together during assembly and the clamping step may include pushing the wedge and the ring together using a pneumatic cylinder. The positioning step may include sliding the wedge into the distal sheath through a non-tapered end of the distal sheath. The method may further include sliding the ring onto the distal sheath after sliding the wedge into the distal sheath.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIGS. 4A and 4B are side and cross-sectional views of a wedge of a distal sheath connector;

FIGS. 5A-5C are side and cross-sectional views of two examples of a ring of a distal sheath connector;

FIG. 7 is a cross-sectional view of an assembled distal sheath connector.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user.

Figure 1:
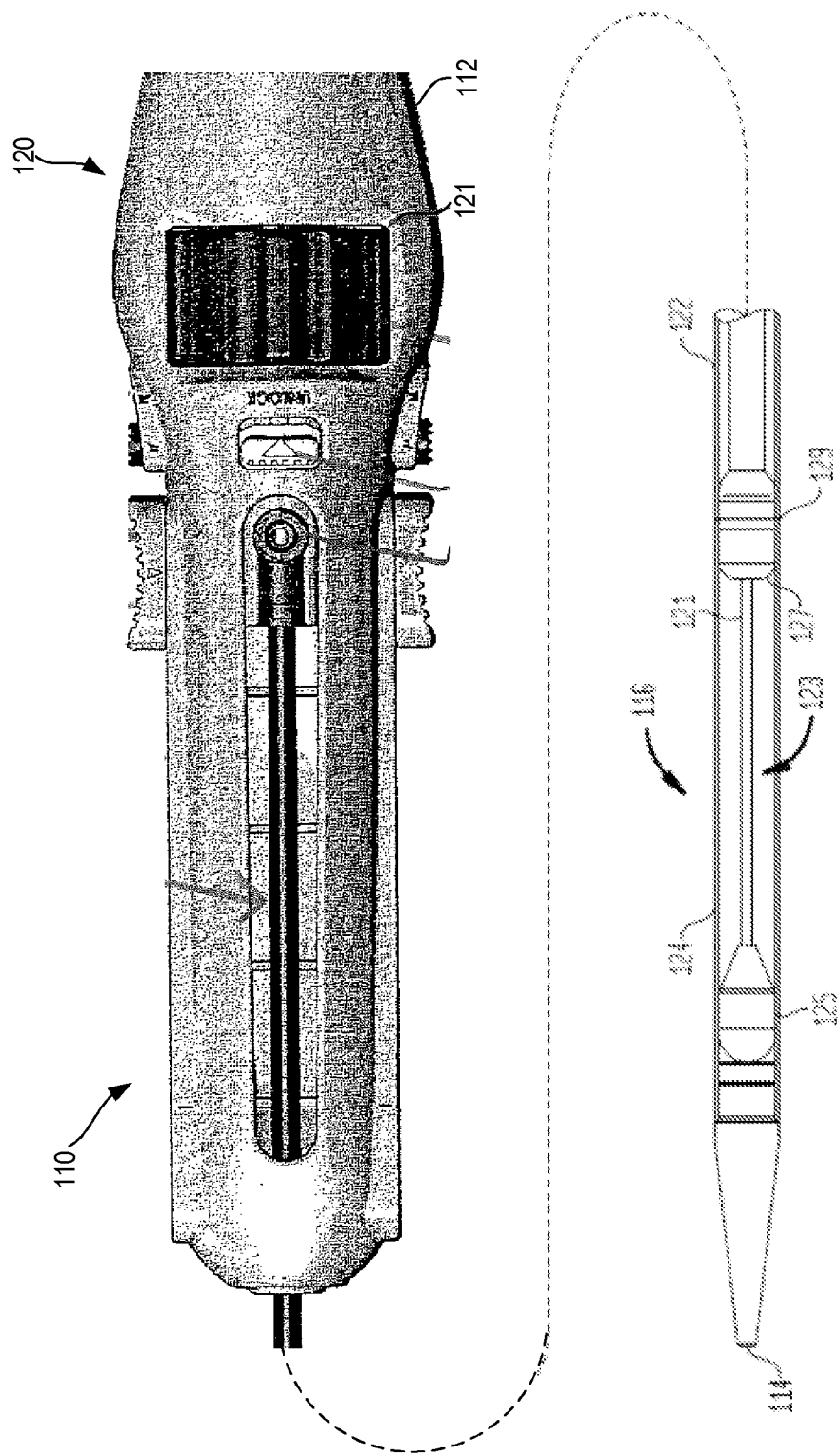
FIG. 1 is a bottom plan view of an operating handle for a transapical delivery device for a collapsible prosthetic heart valve, shown with a side elevation of the distal portion of a transapical catheter assembly.

Referring to FIG. 1, an exemplary transapical delivery device 110 for a collapsible prosthetic heart valve (or other types of self-expanding collapsible stents) has a catheter assembly 116 for delivering the heart valve to and deploying the heart valve at a target location, and an operating handle 120 for controlling deployment of the valve from the catheter assembly. The delivery device 110 extends from a proximal end 112 to a distal tip 114. The catheter assembly 116 is adapted to receive a collapsible prosthetic heart valve (not shown) in a compartment 123 defined around a tubular support shaft 121 and covered by a distal sheath 124.

The support shaft 121 extends between a pair of spaced retainers 125 and 127 affixed thereto and defining the ends of the compartment 123. A collapsible prosthetic valve may be assembled around the support shaft 121 and between the retainers 125 and 127 in the compartment 123.

The distal sheath 124 surrounds the support shaft 121 and is slidable relative to the support shaft such that it can selectively cover or uncover the compartment 123. The distal sheath 124 is affixed at its distal end to the distal tip 114, and its proximal end 129 abuts the retainer 127 when the distal sheath is fully covering the compartment 123, as shown in FIG. 1. The proximal end 129 of the distal sheath 124 is spaced apart from the retainer 127 when the compartment 123 is at least partially uncovered.

The delivery device further includes an outer shaft 122, the proximal end of which is connected to the operating handle 120, and the distal end of which is connected to the retainer 127. An inner shaft 126 extends through the operating handle 120 and the support shaft 121 to the distal tip 114. The connection of the distal sheath 124 to the distal tip 114 thus enables the inner shaft 126 to control the movement of the distal sheath both proximally and distally.

The operating handle 120 is adapted to control deployment of a prosthetic valve located in the compartment 123 by permitting a user to selectively slide the inner shaft 126 and the attached distal sheath 124 distally or proximally relative to the support shaft 121, thereby respectively uncovering or covering the compartment with the distal sheath. The operating handle 120 may include a resheathing lock mechanism for preventing the user from accidentally completing the deployment of a valve located in the compartment 123. Details of the operating handle is described in U.S. Provisional Patent Ser. No. 61/665,527, filed Jun. 28, 2012, the content of which is hereby incorporated by reference in its entirety.

Figure 2:
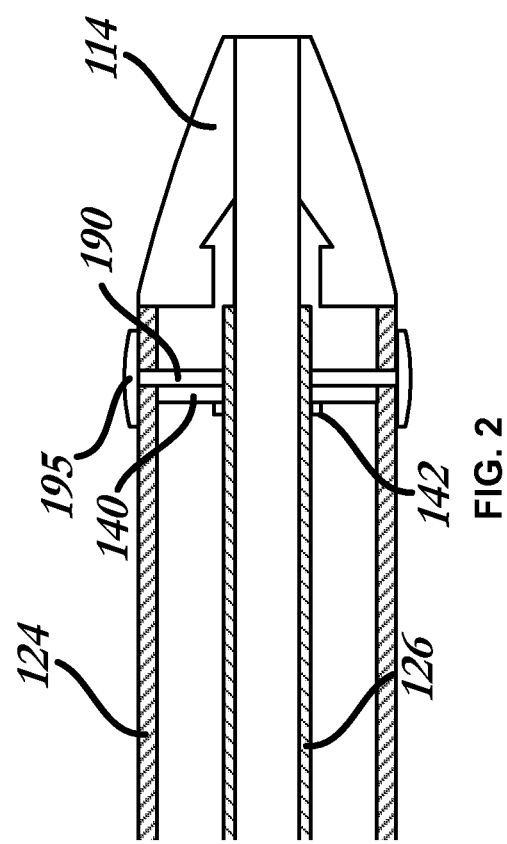
FIG. 2 is an enlarged cross-sectional view of a conventional distal sheath connection having pins.

FIG. 2 is a cross-sectional view of a conventional distal sheath connection having pins. Distal sheath 124 may be attached to nosecone insert 140 through one or more radially extending pins 190. Nosecone insert 140 may be attached to inner shaft 126 by laser welds 142. Pins 190 create a low strength connection between distal sheath 124 and nosecone insert 140 and are difficult to manufacture. In addition, pins 190 may unnecessarily increase the outer diameter of the distal end of the device. Such pins 190 may be trimmed so as to form a flush surface with the distal sheath 124. Pins 190 may further require the use of adhesive 195 to protect the patient from sharp edges.

Figure 3:
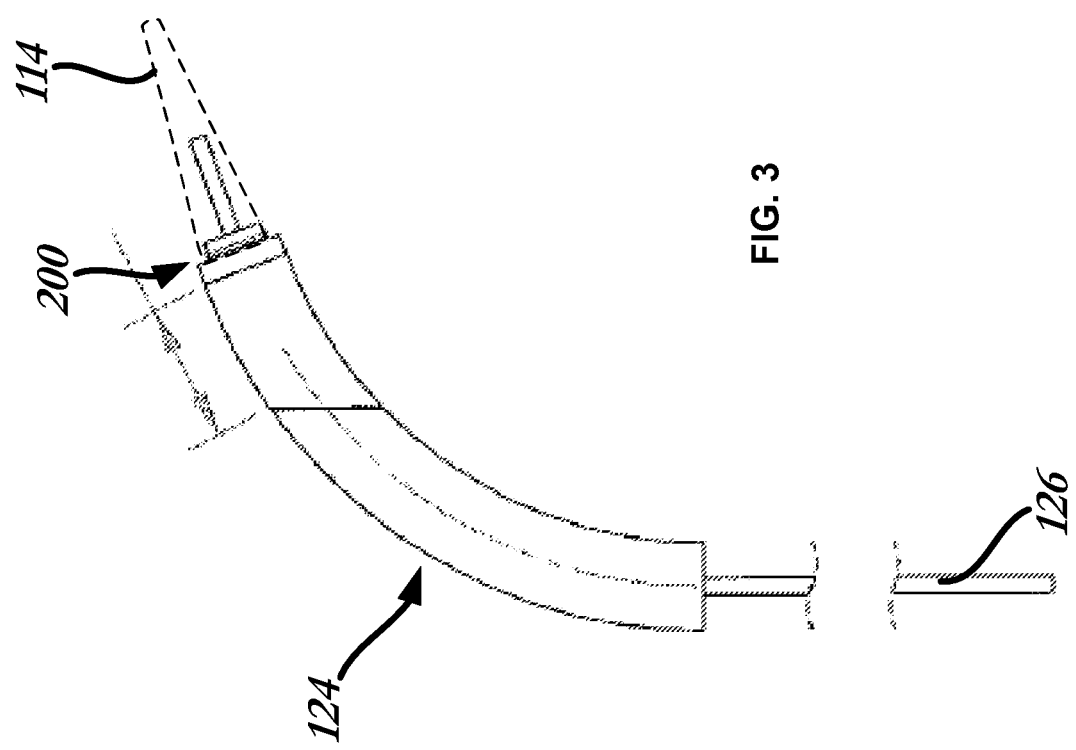
FIG. 3 is an enlarged perspective view of a distal sheath and inner shaft connector.

FIG. 3 is an enlarged perspective view of a distal sheath 124 and inner shaft 126 of the delivery device of FIG. 1 attached to one another using a connector 200. For the sake of clarity, tip 114 is shown in phantom lines to expose the connector. Distal sheath connector 200 forms a durable attachment between distal sheath 124 and inner shaft 126, while maintaining a small diameter and eliminating the need for adhesive to protect the patient from sharp edges as shown in FIG. 2. The components of distal sheath connector 200 will be described in more detail with reference to FIGS. 4A, 4B and 5A-C.

FIGS. 4A and 4B are side and cross-sectional views of a wedge 300 of a distal sheath connector 200. Wedge 300 may be formed of stainless steel or any other suitable metal such as Titanium, Nitinol, platinum, tantalum, gold, silver, cobalt-chromium. Alternatively, wedge 300 may be formed of any suitable biocompatible material including certain plastics and polymers.

Wedge 300 forms the first component of distal sheath connector 200 and sits inside a ring as will be described in further detail below. Wedge 300 may be formed of a substantially cylindrical body having a cone portion 340, and a lumen 330 extending therethrough between a first end 310 and a second end 320. Lumen 330 may be sized to receive inner shaft 126. As seen in FIG. 4A, cone portion 340 may include a series of annular steps 350 such that the outer diameter of the wedge 300 increases from the first end 310 to the second end 320. Annular steps may allow for better attachment to distal sheath 124.

FIGS. 5A and 5B are side and cross-sectional views of a ring 400 of distal sheath connector 200. Ring 400 may be formed of stainless steel or other suitable metals such as those used for wedge 300. Ring 400 and wedge 300 may be formed of the same material. Ring 400 includes a first end 410, a second end 420 and a lumen 430 extending therethrough. Lumen 430 widens to form a taper 450 near second end 420 to complement steps 350 of wedge 300 as will be appreciated from the assembled connector. As shown in FIG. 5C, instead of a taper 450, ring 400 may include a series of concentric recesses 455 sized and shaped to complement annular steps 350 of wedge 300.

Figure 6:
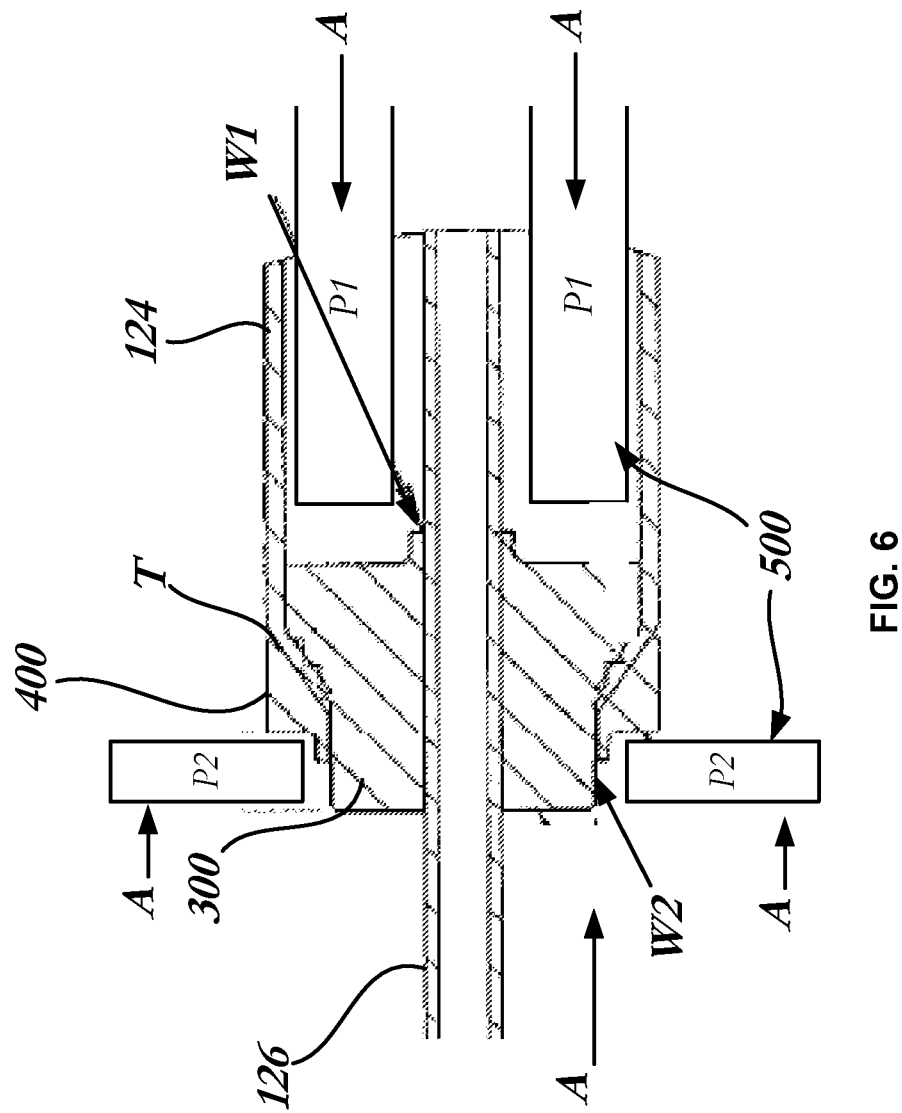
FIG. 6 is a cross-sectional view of a distal sheath connector in a pneumatic cylinder.

FIG. 6 is a cross-sectional view of the distal sheath, inner shaft and distal sheath connector disposed in a pneumatic cylinder during assembly. Wedge 300 may be first mounted on inner shaft 126 and welded to the inner shaft at position W1. This welding may be accomplished using a laser welder. In addition, an end portion T of distal sheath 124 may be thermoformed or tapered inwardly as seen in FIG. 6 using a tipping machine (not shown).

Wedge 300 and inner shaft 126 may be slid into distal sheath 124 through the non-tapered end of the sheath until the steps 350 of the wedge contact the tapered portion T of the sheath. Ring 400 may then be assembled over wedge 300 with tapered portion T of distal sheath 124 disposed therebetween. A pneumatic cylinder may be used to clamp wedge 300, ring 400 and distal sheath 124 together. An exemplary embodiment of pneumatic cylinder 500 includes a first plate P1 and a second plate P2 that apply force to the assembly in the directions shown by arrows A. Plates P1 and P2 move toward one another forcing wedge 300 into and through ring 400 so that the annular steps 350 engage with at least one of concentric recesses 455 of ring 400 and distal sheath 124. Thus, plates P1 and P2 may hold wedge 300 and ring 400 of the connector in place, with the distal sheath partially sandwiched in between. A final weld W2 may be circumferentially made between wedge 300 and ring 400 to permanently fix the two together. In some examples, welds W1 and W2 may be laser welds. Though the preceding example illustrates joining the wedge and ring using welds, it will be understood that any suitable technique for joining the two components may be used including for example, heat staking, impulse sealing, ultrasonic welding, snap fit, press fit, friction welding, vibration welding, hot plate welding and adhesive bonding and may depend on the materials for the wedge and/or ring.

FIG. 7 is a cross-sectional view of an assembled distal sheath connector 200 showing distal sheath 124 sandwiched between wedge 300 and ring 400. Using distal sheath connector 200, distal sheath 124 will more reliably attached to inner shaft 126 and be less prone to failure.

In operation, handle 120 may be used to deploy a prosthetic valve from the compartment 123. Specifically, the user can rotate the deployment actuator 121 to push the distal sheath 124 distally relative to the compartment 123 and expose and initiate deployment of the valve located therein. Once the valve has been properly positioned, the deployment operation may be completed to release the valve from compartment 123.

The operating handles described herein may be provided with a deployment locking mechanism. Such a deployment locking mechanism may prevent the accidental initiation of deployment by fixing the carriage assembly to the frame while the lock is in a locked position. Moreover, the operating handle may include a resheathing lock, or a number of resheathing locks, with or without a deployment lock, resulting in any number of stages in the deployment process. For example, there may be two, three, four, five, six or more resheathing locks, which thus enable the deployment procedure to be controlled incrementally. Such deployment locks and resheathing locks may have a structure similar to those shown and described in co-pending U.S. patent application Ser. No. 13/212,442, filed on Aug. 18, 2011, the content of which is hereby incorporated by reference herein in its entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A connector for coupling a distal sheath and an inner shaft of a medical delivery device, the connector comprising:
    a wedge defining a lumen for accepting the inner shaft of the medical delivery device, at least a portion of the wedge having an outer diameter sized to be received in the distal sheath; and
    a cylindrical ring sized to be disposed over the distal sheath and at least the portion of the wedge;
    wherein engagement of the cylindrical ring with the wedge sandwiches the distal sheath between at least the portion of the wedge and the cylindrical ring to couple the distal sheath and the inner shaft, and wherein the distal sheath is inwardly tapered at a portion sandwiched between the wedge and the cylindrical ring.

2. The connector of claim 1, wherein the wedge includes a cylindrical body and a cone portion.

3. The connector of claim 2, wherein the cone portion of the wedge includes a series of annular steps having increasing diameters.

4. The connector of claim 1, wherein the wedge comprises a biocompatible metal.

5. The connector of claim 1, wherein the wedge comprises stainless steel.

6. The connector of claim 1, wherein the ring defines an outwardly tapering lumen configured to receive the steps of the wedge.

7. The connector of claim 1, wherein the ring and the wedge comprise the same metal.

8. The connector of claim 1, wherein the wedge is welded to the inner shaft.

9. The connector of claim 1, wherein the wedge and the ring are welded together.

10. The connector of claim 1, wherein the connector is configured to couple the distal sheath and the inner shaft in a concentric configuration.

11. A method of coupling a distal sheath having an inwardly tapered portion and an inner shaft of a delivery device, the method comprising:
    providing a connector having a wedge defining a lumen for accepting the inner shaft of the medical delivery device, at least a portion of the wedge having an outer diameter sized to be received in the distal sheath and a cylindrical ring sized to be disposed over the distal sheath and at least the portion of the wedge;
    positioning the inwardly tapered portion of the distal sheath between the wedge and the ring of the connector; and
    coupling the wedge to the inner shaft and the ring so as to sandwich the inwardly tapered portion of the distal sheath between at least the portion of the wedge and the cylindrical ring.

12. The method of claim 11, wherein the coupling step includes laser welding the wedge to the inner shaft.

13. The method of claim 11, wherein the coupling step includes laser welding the ring to the wedge.

14. The method of claim 11, further comprising thermoforming the inwardly tapered portion of the distal sheath prior to positioning the portion of the distal sheath between the wedge and the ring.

15. The method of claim 11, further comprising clamping the wedge and the ring together during assembly.

16. The method of claim 15, wherein the clamping step includes pushing the wedge and the ring together using a pneumatic cylinder.

17. The method of claim 11, wherein the positioning step includes sliding the wedge into the distal sheath through a non-tapered end of the distal sheath.

18. The method of claim 17, further comprising sliding the ring onto the distal sheath after sliding the wedge into the distal sheath.

* * * * *